United States Patent [19]
Hirsch et al.

[11] Patent Number: 5,395,319
[45] Date of Patent: Mar. 7, 1995

[54] NEEDLE FOR INSERTING AN OBJECT INTO THE BODY

[75] Inventors: Christian Hirsch, Bruchköbel; Herbert Feit, Wächtersbach, both of Germany

[73] Assignee: Suddeutsche Feinmechanik GmbH, Germany

[21] Appl. No.: 117,066

[22] PCT Filed: Feb. 29, 1992

[86] PCT No.: PCT/EP92/00444
§ 371 Date: Jan. 4, 1994
§ 102(e) Date: Jan. 4, 1994

[87] PCT Pub. No.: WO92/15362
PCT Pub. Date: Sep. 17, 1992

[30] Foreign Application Priority Data

Mar. 6, 1991 [DE] Germany .................. 41 07 042.9
Oct. 15, 1991 [DE] Germany .................. 9112797 U
Dec. 18, 1991 [DE] Germany .................. 9115658 U

[51] Int. Cl.⁶ .................. A61M 31/00; A61M 5/32
[52] U.S. Cl. .................. 604/60; 604/199
[58] Field of Search .................. 604/57, 59, 60, 61, 604/63, 199, 239, 272, 274; 206/828

[56] References Cited

U.S. PATENT DOCUMENTS

| 2,601,852 | 7/1952 | Wendt | 604/59 |
| 2,761,446 | 9/1956 | Reed | 604/59 |
| 4,451,253 | 5/1984 | Harman | 604/60 |
| 4,820,267 | 4/1989 | Harman | 604/60 |
| 4,950,234 | 8/1990 | Fujioka et al. | 604/60 |

FOREIGN PATENT DOCUMENTS

| 0531807 | 1/1958 | Italy . | |
| 0252587 | 6/1926 | United Kingdom | 604/60 |

Primary Examiner—C. Fred Rosenbaum
Assistant Examiner—Frank Wilkens, III
Attorney, Agent, or Firm—Bierman and Muserlian

[57] ABSTRACT

Proposed is a needle (12) with a sharpened point (14) at the tip and a needle holder (16) at the rear end holding the needle, a mandrel (24) which can be displaced inside the needle, and optionally a protective cap (18) enclosing the needle point and detachably attached to the needle holder, with which objects (10) such as longterm preparations, identification tags, or the like are to be inserted in the body of a living being. To ensure that the object is unequivocally fixed in position inside the needle, the object is arranged between a closure toward the tip of the needle and, for example, a constriction (20) toward the handling end. The closure is preferably a stopper which is carried along with the object when the latter is inserted.

19 Claims, 5 Drawing Sheets

NEEDLE FOR INSERTING AN OBJECT INTO THE BODY

FIELD OF THE INVENTION

The invention concerns a needle with a sharpened point at the tip and a needle holder at the rear end holding the needle, a mandrel which can be displaced inside the needle, and optionally a protective cap enclosing the needle point and detachably attached to the needle holder, preferably in the form of a hollow cylindrical element open at one end, designed to insert an object in the body of a living being by interaction and relative movement of the mandrel and needle.

BACKGROUND OF THE INVENTION

It is a known process to implant electronic identification carriers such as microtransponders or chips to identify animals, for which purpose the electronic identification carrier is inserted under the animal's skin tissue. This is done with a needle in which the transponder is arranged displaceably. The needle is first introduced under the skin tissue. The needle is then slowly withdrawn; a mandrel present inside the needle and displaceable with respect to it causes the transponder or chip to be inserted into the animal's flesh as the needle is withdrawn. The needle is therefore moved with respect to the essentially stationary mandrel. A pistol-like handle can be used for this purpose, as indicated for example by GB 2 190 590 A. At the moment the identification carrier is inserted, the front tip of the mandrel is in or in front of the needle opening, so that the mandrel comes into contact with the living being's tissue or blood. This also creates the risk of inflammation of the tissue.

Needles for inserting solid or semisolid preparations under the skin of a human being are indicated, for example, by U.S. Pat. No. 4,900,304, U.S. Pat. No. 4,950,234, or EP 0 255 123 A2. EP 0 304 107 A1 describes an injection needle for inserting an implant. The needle is designed for one-time use.

The needle, which can be attached to the handle, is always in a sterile package (known in the art), which when the needle is used must be torn open so the needle can then be removed. Depending on the kind of package, a relatively large amount of packaging material occurs relative to the size of the needle. Packaging and unpacking are also laborious.

SUMMARY OF THE INVENTION

The underlying problem of the present invention is to develop a needle of the aforementioned kind in such a way that is can be used easily and, in particular, without complex or expensive auxiliaries. The intent is to guarantee that the object is located in a previously known position inside the needle, thus simplifying implantation.

The object should also be immobilized inside the needle in such a way that damage during transport, due for example to uncontrolled shifting back and forth inside the needle, does not occur.

Another purpose is to ensure there is no risk that living beings will be infected when the needle is used.

Lastly, universal utility and simplifications in the packaging of sterile needles are striven for, as is a reduction in waste.

According to the invention, the problem is substantially solved by the fact that the object is fixed in position, before insertion into the body, between the mandrel and the needle point, the object being fixed in position at the needle point end by a closure which can be destroyed or removed by the object when it is inserted, and which closes off at least a region of the needle.

The invention guarantees unequivocal fixed positioning of the object, thus ensuring defined insertion into the body.

At the needle point end, at least a region of the lumen of the needle can be closed off by a ointment-like material containing a medicinal active ingredient, which remains adhering at least to regions of the object during insertion. This provides at least a preventive measure against inflammation.

The closure can also, however, be for example an adhesive material or a silicone stopper.

At the holder end, fixed positioning is achieved by means of a change in cross section, such as a reduction in the cross section of the lumen.

The change in cross section serves as the same time as a limitation in displacement travel for the end region of the mandrel facing away from the needle point. This ensures that the rear end of the mandrel can be pushed only as far as the reduction in cross section, ensuring that when the needle is removed from the tissue, the mandrel always remains in the needle.

The change in cross section itself can be formed, for example, by at least two indentations, such as bumps, extending diametrically to the long axis of the needle, thus additionally guiding the mandrel inside the needle. This ensures that the mandrel, which is preferably made of plastic, is not bent in an uncontrolled fashion inside the needle.

Instead of an indentation and bump or the like, a reduction in cross section can also be formed by a circumferential, or optionally only partially circumferential, bead.

Fixing the position between the closure and the change in cross section thus ensures that, in particular during transport, uncontrolled or undesired lengthwise shifting back and forth inside the needle does not occur.

The following must also be noted with respect to the closure at the needle point. When adhesive material is used, it should have, with respect to the needle, adhesive properties which, when the material is penetrated by the object or the mandrel, ensure that the adhesive material remains adhered within the needle.

The closure material, which preferably is to be applied in a noncontact manner into the needle, for example by dripping it in, should, because of adhesion, produce at least an annular reduction in cross section of the lumen of the needle; optionally a skinlike closure is formed in the region of the long axis, thus completely shielding the object from the outside.

The invention further provides that, in order to displace the mandrel toward the needle point, there be insertable into the needle a pin element such as a steel pin, which in turn preferably extends from the protective cap enclosing the needle.

According to a further proposal of the invention, the protective cap can be a cylindrical element open at one end, the inside diameter of the cylindrical cap corresponding to the outside diameter of the needle holder.

When the object is implanted, the needle holder is displaced inside the protective cap, with the result that the pin projecting from the bottom surface of the protective cap penetrates into the needle, so that when the needle is withdrawn from the tissue—i.e. when the needle is displaced toward the bottom surface of the protective cap—the mandrel is displaced toward the needle point, so as thereby to ensure that the object can be inserted in the tissue.

When the protective cap is to perform the actual function of the protective cap, the needle passes through it from the outside of the bottom surface, specifically in a perforation that runs eccentrically. In this case the needle runs parallel to the pin element and extends inside the protective cap, which can be welded in together with the handle, for example in a packaging material.

In order for withdrawal of the needle to occur in a controlled manner, weblike handles, which are guidable in lengthwise slits of the protective cap, can project from the needle holder. To keep the needle from sliding out of the handle in an uncontrolled manner, the respective lengthwise slit is preferably designed with steps.

An independent proposed solution provides for the needle holder to have, in the region adjacent to the needle, a hollow cylindrical enlargement to whose inside diameter a plate-shaped section of the mandrel is matched; and for the hollow cylindrical enlargement to be designed to displaceably receive a sliding element, the sliding element preferably being the protective cap itself.

The invention proposes a needle for the implantation of objects, in which the mandrel is designed as a piston or ram, that can be acted on, in the needle holder which has the function of a cylinder, by means of the sliding element, which can also be installed in the cylindrical enlargement. With these features, the mandrel can be inserted into a tissue, without great exertion and using the protective cap as a pusher element, exclusively with the objects necessary for the needle. As with the known needles, the needle is pulled out of the tissue, so that the identification carrier is implanted in the flesh while the mandrel remains almost stationary.

To ensure that the protective cap can be easily installed into the hollow cylindrical enlargement of the needle carrier, the closed end, i.e. the one enclosing the needle point, is tapered with respect to the remaining section, which is matched to the inside diameter of the enlargement.

To ensure interaction between the protective cap and the piston, i.e. the plate-shaped section of the mandrel, the closed end of the protective cap is designed, at least in certain regions, to be complementary to the external surface of the plate-shaped section. Preferably the protective cap has a flat end surface, so that consequently the external surface of the plate-shaped section which performs the piston function is also flat.

The fact that the rims surrounding the openings of the protective cap and needle holder have sections bent outward makes it easy to push the protective cap into the hollow cylindrical enlargement of the needle holder.

To simplify the packaging of the needle and to reduce waste, an independent proposed solution provides for the needle to extend completely inside the protective cap, which is provided at its open end with a flexible covering; for the protective cap to have at least two sections of different cross section, of which a front (first) section enclosing the needle point is arranged with its region facing away from the needle point on the needle holder; and for an end (second) section to be at one end sealed with the flexible covering and at the other end separably attached to the first section.

According to the invention, the protective cap consequently serves not only as protection for the needle point, but also at the same time as a sterile package, so that these simplifications are provided both when the needle itself is packaged and when it is unpacked. In particular, the packaging process that would otherwise be necessary becomes superfluous, since with the application of the protective cap, the packaging itself is made available. All that is then necessary is to close off the open end, extending in the region of the needle holder, with a flexible covering such as paper.

When the needle is used, there is the resulting advantage that compared with otherwise known packages, only the covering of the protective cap of the rear section of the protective cap becomes waste, while the remaining part of the package, i.e. the protective cap itself, is handled in the usual way.

For reasons of economy of materials in particular, the front section of the protective cap, for its part, can be composed of regions of different cross section, the region surrounding the needle holder having a larger cross section compared with the region surrounding the free needle.

In order to handle the needle in the usual way, it is furthermore provided, on the one hand for the second section to surround the needle holder at a distance, and on the other hand for there to be a defined break point between the first and second section.

In this context, a weblike partition, connecting the first with the second section, can extend from the end region of the second section that faces the first section.

Alternatively, it is possible for the outside diameter of the first section, in the attachment region between the first and second sections, to correspond approximately to the inside diameter of the second section, thus forming a circumferential breakaway edge.

According to a further proposal of the invention, a circumferential notch can extend in the first section in the transition region between the first section and the second section, to form a defined break point.

The needle according to the invention is not intended only for use in veterinary medicine; it can also be used in the human medical field. For this purpose the object can be designed as or can contain, for example, a long-term medicinal preparation, a capsule containing radioactive substances, or a metallic contrast element.

Possible long-term medicinal preparations include, for example, contraceptive preparations or morphine preparations.

Utilization in accordance with the invention results, especially with respect to capsules containing radioactive substances, in the advantage that implantation can occur more specifically in those regions of the body that are to be treated.

Further details, advantages, and features of the invention are evident not only from the Claims and the features contained therein, individually and/or in combination, but also from the description below of the preferred exemplary embodiments that are evident from the drawings.

DETAILED DESCRIPTION OF THE PREFERRED EMBODIMENT

Figure 1:
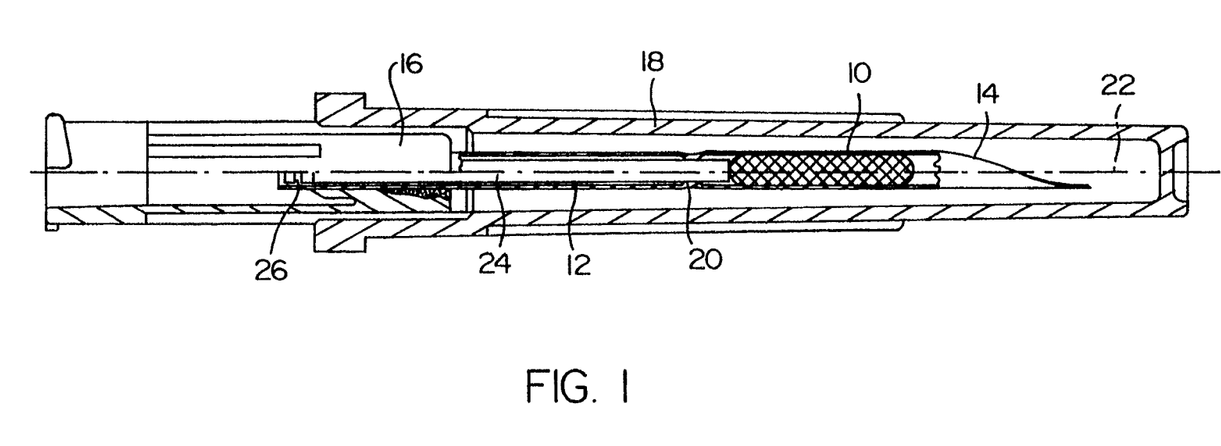
FIG. 1 shows a cross-section through a needle for implanting objects.

A needle (12) is used to implant in an animal or human being an object—such as an identification carrier, a long-term medicinal preparation, contrast metal, or an encapsulated radioactive preparation—very generally designated (10) in FIG. 1.

The needle (12) can be a steel needle, plastic needle, or a needle made of another suitable material, with an obliquely sharpened point (14). The needle (12) is received in a needle holder (16). Extending detachably from the needle holder (16) is a protective cap (18) that encloses the needle (12).

The needle has, at a distance from the point (14) and the needle holder (16), a constriction (20) that can be formed, for example, by two bumps arranged diametrically with respect to the long axis (22) of the needle, or by a bead over at least portions of the circumference. The cross section in the region of the constriction (20) is hence less than the diameter of the identification carrier (10), thus ensuring that the latter cannot slide out beyond the constriction (20) toward the needle holder (16).

A mandrel (24) is also arranged displaceably in the needle (12), specifically from the needle holder (16) side. The mandrel has, in the end region facing away from the needle point (14), a thickened cross section such as a circumferential ridge (26), the diameter of which is greater than that of the constriction (20). This ensures that the thickening (26) cannot pass through the constriction (20).

In order for the object (10) to be insertable in a tissue (not shown), a pin element, configured in any manner, with a diameter less than the diameter of the lumen of the needle (12), acts on the mandrel (26) so that when the needle (12) is withdrawn, the mandrel (24) remains in its position, with the result that the object (10) enters the tissue. In the process, the front end of the mandrel (24) may come into contact with the tissue. This is not harmful if the mandrel (24), together with the needle (12) and its holder (16), constitutes a disposable unit. Otherwise sterilization must occur.

The pin element of a handle (not depicted) acting on the mandrel (24) can be repeatedly reused with no need for sterilization, since there is no contact with the tissue.

Figure 4:
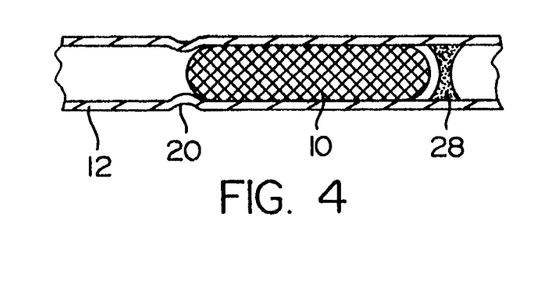
FIG. 4 shows an enlarged section of the needle according to FIG. 1.

As illustrated by FIG. 4, the object (10) is fixed in position in the needle (12) at the holder end by the constriction (20) and at the needle point end by a closure (28), which can be formed by a drop of adhesive dripped into the needle. The adhesive material has an adhesion to the needle material such that, when it is penetrated by the identification carrier (10) and the mandrel (24) (not depicted), the material does not adhere to it, but only to the needle wall. The adhesive material then coheres into a kind of droplet shape.

Although in the exemplary embodiment of FIG. 4, the closure (28) is depicted as covering the entire cross section, this is not a mandatory feature. Instead it is sufficient if the closure is implemented with a thickening of adhesive material extending annularly along the inner wall of the needle (12). Optionally, the cross section can also be closed by a thin skin of adhesive material.

Preferably, however, the closure (28) is formed by an ointment-like material containing a medicinal active ingredient, which can again be dripped into the needle. The material has adhesive properties with respect to the object (10) such that adhesion to it occurs. As a result the medicinal active ingredient also enters the tissue, so that any inflammations can be prevented. A poly(1-vinyl-2-pyrrolidone)iodine complex preferably serves as the active ingredient. The material can also contain polyethylene glycol in the form of an ointment.

Figure 2:
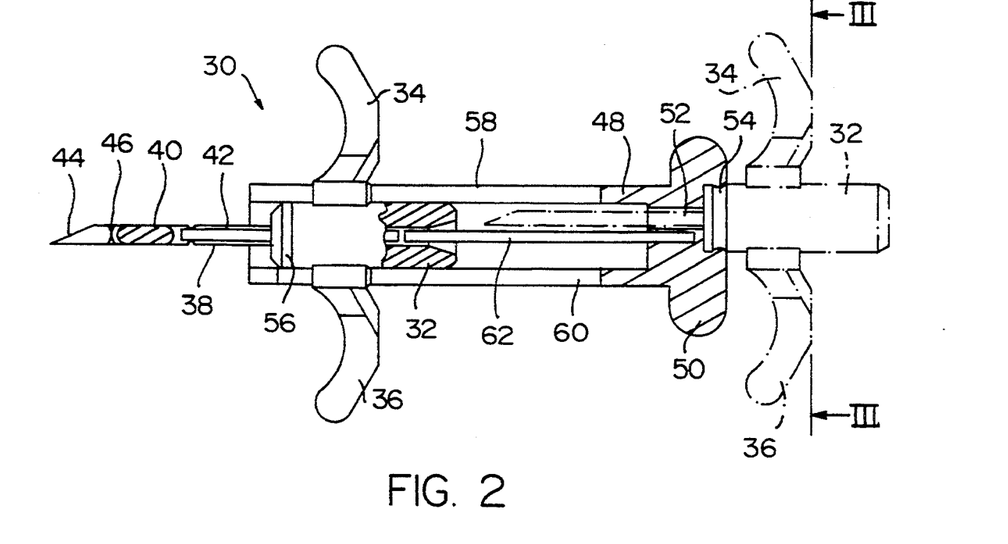
FIG. 2 shows a cross-section through an implanter with a needle according to FIG. 1.
Figure 3:
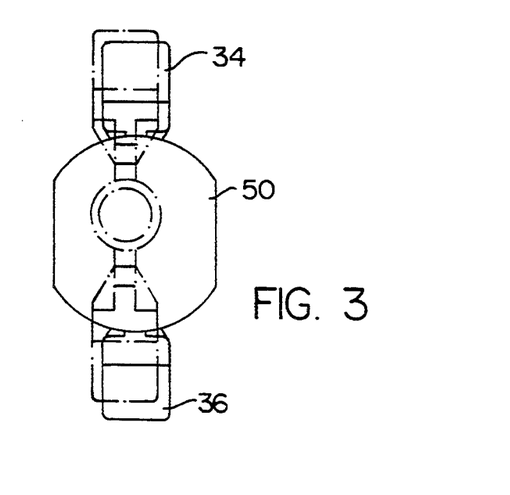
FIG. 3 shows a view along line III—III in FIG. 2.

FIGS. 2 and 3 depict a single-use implanter (30). The single-use implanter (30) has a needle holder (32) with projecting handle elements (34) and (36). Extending from the needle holder (32) and passing centrally through it is a needle (38), which corresponds to the configuration of the needle (12). Consequently an object (40) is arranged in a fixed position in the needle (38). Fixed positioning is achieved on the one hand by means of a partial reduction in the cross section of the needle lumen, and on the other hand by means of a droplet or ring (46) arranged at a distance from the needle point (44).

In the unused state, the needle (38) is surrounded by a protective cap (48). The protective cap (48) is a cylindrical element, closed at one end and open at the needle point end. The bottom or base section (50) of the protective cap (48) has flange-like extensions. Extending eccentrically in the base section (50) is a bore (52) that continues on the outside into a cylindrical expansion (54) whose diameter corresponds to the outside diameter of the needle holder (32) in the region (56) adjacent to the needle (40). This region (56) can have step-shaped sections that are also encountered in the depression (54). As a result, snap locking can occur between the protective cap (48) and the needle holder (32) when the needle (38) is extending inside the protective cap (48), i.e. when the protective cap (48) is performing the actual function of protection for the needle (38).

The inside diameter of the protective cap (48) corresponds to the outside diameter of the needle holder (32). When the object (40) is to be inserted in a tissue, the handle (32) is introduced from the front into the protective cap (48). Slit-shaped guides (58) and (60), whose respective width corresponds to that of the handle elements (34) and 36) are provided for this purpose in the wall of the protective cap (48). The slits or guides (58) and (60) have a stepped profile to prevent the needle holder (32) with the needle (38) from inadvertently sliding out of the protective cap (48).

Extending from the inside of the base section (50) is a pin element such as a steel pin (62) which, when the needle holder (32) is installed in the protective cap (48), extends along the long axis of the needle (38) and penetrates into it. The diameter of the pin (62) is less than the inside diameter of the needle (38). When the needle holder (32) is pulled, by means of the handle elements (34) and (36), toward the base of the protective cap (48), the steel pin (62) is thereby forced into the needle (38) so as to displace a mandrel(42) apparently in the direction of the needle point (44), so that the object (40) can be carried along and thereby inserted in a tissue.

The dashed-line depiction of the needle holder (32) with the handle elements (34) and (36) is intended to indicate the position in which the protective cap performs its actual function, i.e. in which the needle passes through the perforation (52) in order to be protected by the protective cap (48). The extension of the needle inside the protective cap (48) is then less than the inside depth of the protective cap (48) itself.

Figure 5:
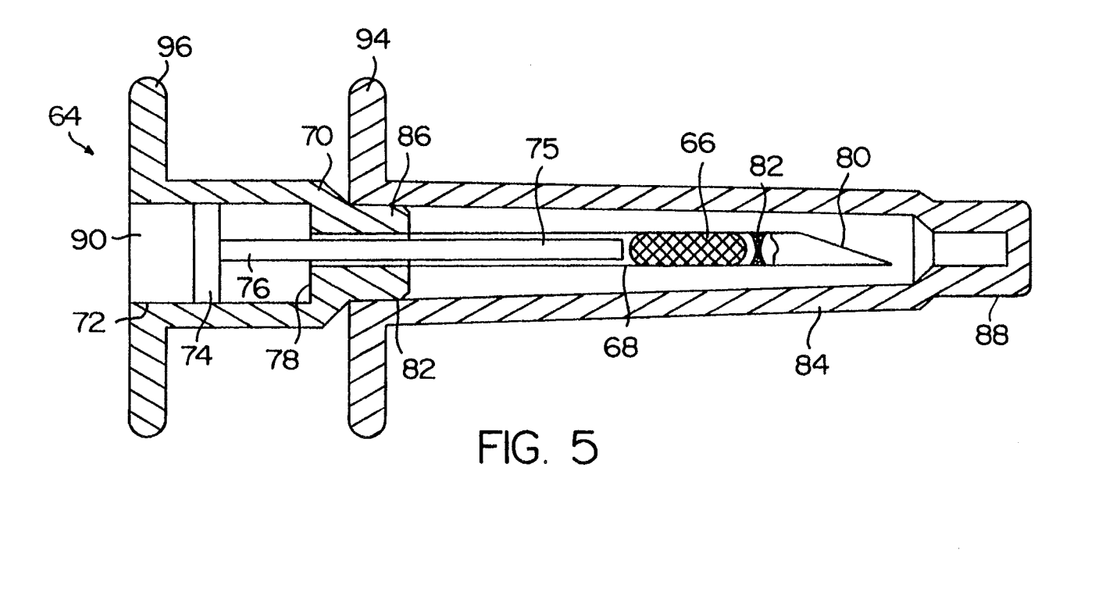
FIG. 5 shows a further embodiment of an implanter.

FIG. 5 shows a sectional depiction through a further embodiment of an implanter (64) for implanting an object (66) such as a transponder.

The implanter (64) comprises a needle (68) that is received by a needle holder (70) which in turn has, outside the needle (68), a hollow cylindrical enlargement (72) that hereinafter will be described as acting as the cylinder for a piston.

Located inside the needle (68) is a displaceable mandrel (75) that has externally a plate-shaped section (74), matched to the inside diameter of the hollow cylindrical enlargement (72), which is consequently the piston. The section (76) extending from the piston (74) which can be displaced inside the needle (68), i.e. essentially the piston rod, has a length which is sufficient, when the piston (74) is pushed to the bottom (78) of the hollow cylindrical enlargement (72), to allow insertion of the object (66), such as a transponder, medicinal preparation, or the like, through the opening (80) of the needle (68) in a tissue.

The object (66) is immobilized by means of a silicone stopper, adhesive stopper (82), viscous material containing a medicinal active ingredient, or the like, located in the region of the opening (80) of the obliquely sharpened needle (68).

On the outside, the needle (68) is covered by a protective cap (84) that can slide on a tapered section (86), enclosing the needle (68), of the needle holder (70). The protective cap (84) and needle holder (70) can be configured as a single unit and with a defined break point in the region of the taper (86), in order to prevent inadvertent removal of the protective cap (84); at the same time, it is possible to check whether or not the needle is still sterile.

According to the invention, the protective cap (84) performs not only the function of protecting the needle (68), but at the same time can serve as an auxiliary tool for displacing the mandrel (75) toward the needle opening (80), i.e. for pushing the object (66) into the tissue.

The protective cap (84) has a cylindrical shape whose outside diameter is matched to the inside diameter of the hollow cylindrical enlargement (72). The protective cap (84) can consequently perform the function of a plunger, acting on the piston (74) and thus on the mandrel (75) in order to displace it inside the needle (68).

To allow easy penetration of the protective cap (84) into the hollow cylindrical enlargement (72), the protective cap (84) has a tapered section (88) in its closed region.

To facilitate displacement of the protective cap (84) into the hollow cylindrical enlargement (72), i.e. to make the needle holder (70) and protective cap (84) easier to grasp when they are displaced with respect to one another, the opening (90) of the needle holder (70) and the opening (92) of the protective cap (84) have rim sections (94) and (96) bent outward, which do not, however, need to be made circumferential; diametrically opposite sections pointing outward are sufficient.

Embodiments of protective caps particularly worthy of emphasis, which simultaneously perform the function of a sterile package will be explained with reference to FIGS. 6 to 9.

The needle (112) depicted in FIG. 6 can again be a steel needle, plastic needle, or a needle made of another suitable material, with an obliquely sharpened point (114). The needle (112) is received by a needle holder (116). A protective cap (118), which encloses the needle (112) over its entire length and thus receives it, is provided detachably with the needle holder.

Figure 6:
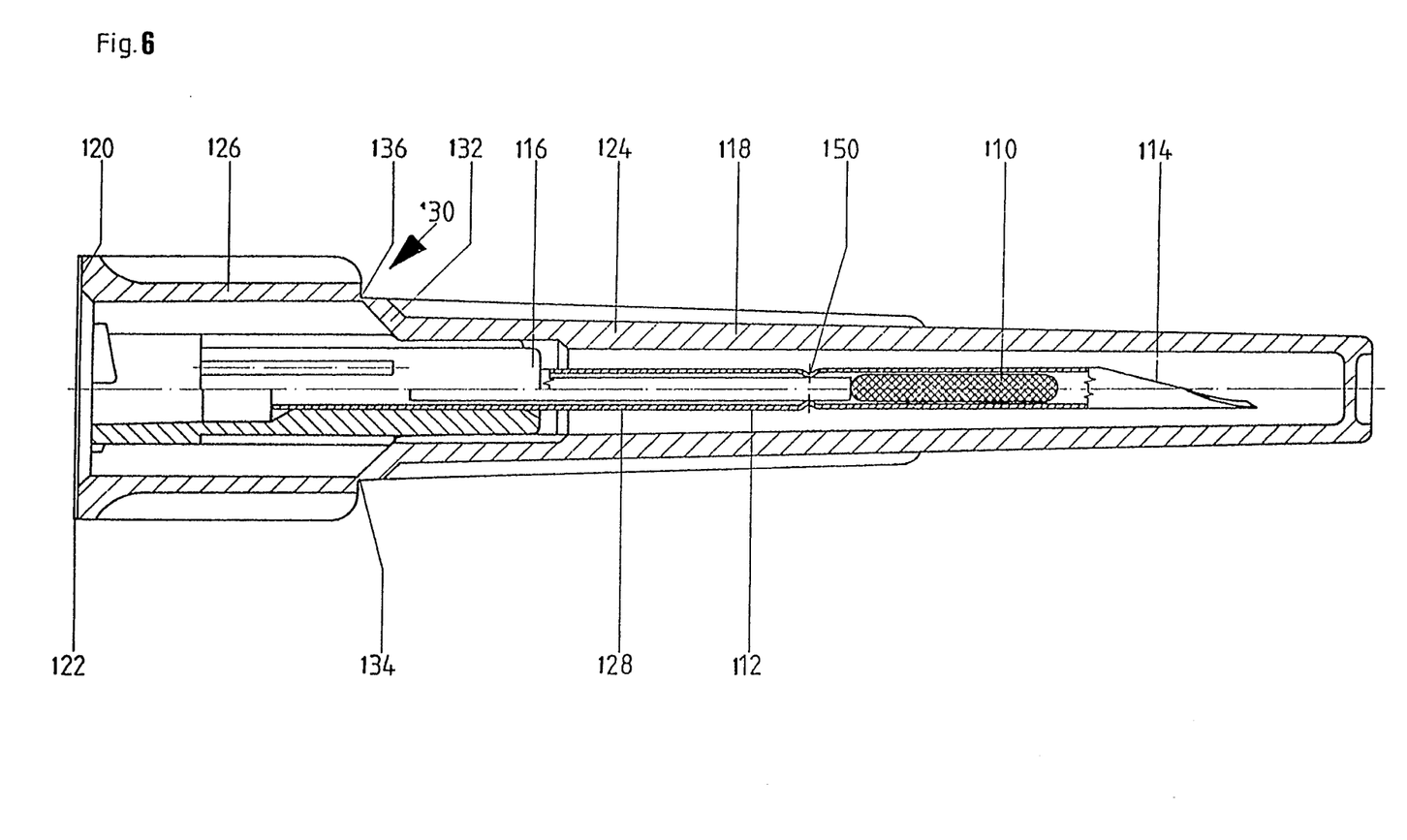
FIG. 6 shows a further embodiment of a needle for implanting an object a tissue, with a protective cap enclosing the needle, in section.

An object (110) to be inserted in a tissue is arranged in a fixed position and displaceably in the needle (112).

The protective cap (118) is consequently a hollow cylindrical element inside which the needle (112), including its needle holder (116), extends. The protective cap (118) is closed at its free end region (120) by a flexible covering such as paper (122). The protective cap with the covering (122) consequently yields a package for the needle (112).

The protective cap (118) is composed of two sections (124) and (126). The front section (124) surrounds the free region (128) of the needle (112) and is arranged detachably on the needle holder (116). Consequently the section (124) in the region enclosing the needle holder (116) has an inside cross section that is matched to the outside cross section of the needle holder (116).

The section (124) can taper toward the needle point (114). A step, and a change in cross section associated therewith, can also be configured in the transition region from the region surrounding the needle holder (116) to the region surrounding the free needle (128).

The second section (126) of the protective cap (118) facing away from the needle point (114) has a larger cross section compared with the first section (124), and thus a greater inside width. The section (126) thus surrounds the needle holder (116) at a distance.

In order, in particular, to allow removal of the section (126) while the section (124) remains on the needle holder (116), a defined break point is configured in the transition region, indicated in FIG. 6 with the reference number (130). In this region the front section (124) has a conical enlargement (132). The diameter of the free outer rim (134) of the conical enlargement (132) is approximately equal to the inside diameter of the adjacent second section (126) of the protective cap (118). This forms a circumferential breakaway edge (136) that exhibits the function of the defined break point.

Of course it is not necessary for the front section (124) of the protective cap (118) to exhibit the conical enlargement (132). Instead the section (124) can be beveled in its end region (138) facing the end section (126) (FIG. 7), thus forming a weblike transition region (140) to the inner wall surface (142) of the section (126).

Figure 7:
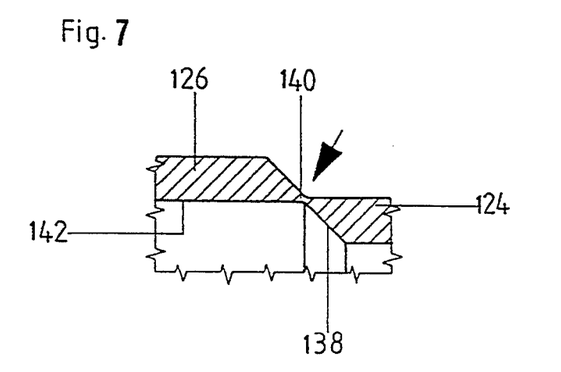
FIG. 7 shows section of the protective cap according to FIG. 6.

This again forms a defined break point in the form of a circumferential weblike partition, the thickness of which depends on the difference between the outside diameter of the section (124) and the inside diameter of the section (126) of the protective cap (118).

Figure 8:
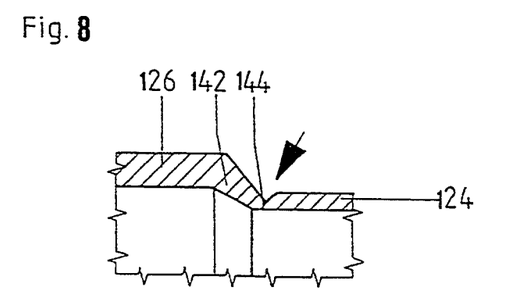
FIGS. 8 and 9 show sections of further embodiments of protective caps.
Figure 9:
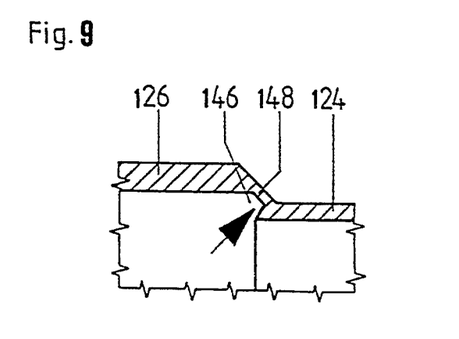

FIGS. 8 and 9 indicate further embodiments of defined break points between the front section (124) and rear section (126).

According to the exemplary embodiment of FIG. 8, for example, a circumferential constriction or notch (144) is provided in the wall of the section (124) at a distance from the transition region (140) between the sections (124) and (126).

According to FIG. 9, there extends toward the section (124), from the end region (146) of the rear section (126) facing section (124), a weblike connecting partition (148) that again performs the function of a circumferential breakaway edge and thus of a defined break point.

According to the teaching of the invention, the protective cap (118) performs a double function. On the one hand it serves in the usual manner as protection for the needle point (114). At the same time, the protective cap (118) is a disposable package, since it is necessary only to seal the rear free end surface with a preferably flexible material such as paper, after the needle has been installed in the protective cap (118). Despite this double function, however, handling of the needle is not impaired, since the presence of the defined break points allows easy removal of the rear part of the protective cap, i.e. section (126), so the needle with the needle holder can then be fastened in, for example, a pistol-like handle.

As is moreover evident from FIG. 6—as in the exemplary embodiments described previously—the needle (112) has, at a distance on the one hand from the point (114) and on the other hand from the needle holder (116), a constriction (150) that can be formed, for example, by two bumps arranged diametrically with regard to the long axis of the needle, or by a bead that is at least partially circumferential. The cross section in the region of the constriction (150) is then less than the diameter of the object (110), ensuring that the latter cannot slide out beyond the constriction (150) toward the needle holder (116).

Furthermore a mandrel (not depicted) is displaceably arranged in the needle, specifically from the needle holder side. In the end region facing away from the needle point (114), the mandrel has a thickened cross section such as a circumferential ridge, the diameter of which is greater than that of the constriction (150). This ensures that the thickening cannot pass beyond the constriction (150).

To allow the object (110) to be inserted in a tissue (not depicted), a pin element configured in any manner, with a diameter less than that of the lumen of the needle (112), acts on the mandrel in such a way that when the needle is withdrawn, the mandrel remains in its position, so that the object (110) can be inserted in the tissue.

To define further the position of the object (110) between the constriction (150) and the needle point (114), a closure stopper (not depicted), which is removed and/or partially carried along when the object (110) is inserted, can be provided between the mandrel and the needle point (114). The closure stopper can be, for example, a silicone stopper or also a medicinal preparation, so as to evoke a curative effect in the event of any damage to the tissue occurring during implantation.

We claim:

1. A device for introducing a solid material into a body comprising an elongated needle having a lumen axially therethrough and a point at its distal end, a proximal end of said needle remote from said distal end, said proximal end in a needle holder, a mandrel at least partially in said lumen and complementary thereto, said mandrel having first end nearer said distal end and a second end remote from said distal end, said mandrel adapted to slide axially in said lumen, said solid material releasably fixed in said lumen between said point and said first end of said mandrel, a yieldable first closure in said lumen between said point and said solid material.

2. The device of claim 1 wherein said first closure is selected from the group consisting of silicones, adhesives, and substances containing active medicinals.

3. The device of claim 1 comprising a protective cap enclosing said point and detachably connected to said needle holder.

4. The device of claim 1 comprising a second closure between said solid material and said first end of said mandrel.

5. The device of claim 2 wherein said second closure is a constriction in said lumen.

6. The device of claim 2 wherein said adhesive adheres to said lumen after penetration by said solid material.

7. The device of claim 2 wherein said medicinal contains a polyiodine complex.

8. The device of claim 2 wherein said medicinal, upon penetration thereof by said solid body, adheres thereto.

9. The device of claim 4 wherein said constriction is at least two radially inwardly extending protuberances in said lumen, or a radially inwardly extending, at least partially circumferential, bead in said lumen.

10. The device of claim 1 comprising a protective cap enclosing said point and surrounding said needle holder, said cap having a closed end adjacent said point and an open end remote therefrom, and a removable seal on said open end.

11. The device of claim 10 wherein said seal is flexible, said protective cap comprises a distal section enclosing said point and a proximal section surrounding said needle holder, a bore extending axially through said distal section and said proximal section, said bore having a distal diameter in said distal section and a proximal diameter in said proximal section, said proximal diameter being larger than said distal diameter, said distal section and said proximal section being connected by a transition section extending from said distal diameter to said proximal diameter, said distal section being detachable from said proximal section.

12. The device of claim 11 comprising a break point in or adjacent said transition section.

13. The device of claim 11 wherein an outside diameter of said distal section corresponds approximately to said proximal diameter.

14. The device of claim 12 wherein said break point is a circumferential notch.

15. The device of claim 1 wherein said solid material is selected from the group consisting of an identifier, a long-term medication, a radioactive substance, and a metallic contrast element.

16. The device of claim 1 comprising a generally cylindrical protective cap having an interior hollow portion and an internal diameter substantially equal to an external diameter of said needle holder, said cap having a receptacle on an external surface with a channel extending from said receptacle to said hollow portion, said receptacle and said channel being parallel to and separated from an axis of said cap, an axial pin on said cap extending into said hollow portion,
when said device is in a protected configuration, at least part of said cap is in said receptacle and said needle extends through said channel into said hollow portion.

17. The device of claim 16 wherein, when in an operative configuration, said needle holder is within said hollow portion and said needle extends out of said portion, whereby movement of said holder toward said external surface causes said pin to contact said mandrel to urge said solid material out of said needle.

18. The device of claim 17 wherein there are a pair of lateral elements on said needle holder extending perpendicular to said axis and on opposite sides of said needle holder, a pair of slits, complementary to said lateral elements in said cap, whereby said needle holder carrying said lateral elements can move along said axis when in said operative position.

19. The device of claim 1 comprising a generally cylindrical protective cap having an interior hollow portion, a closed end with a cap external diameter, and an exposed end remote from said closed end, said exposed end having a cap internal diameter, said needle holder having a projection of approximately equal diameter to said cap internal diameter from which said needle axially extends, an enlarged opening in said needle holder open in a direction away from said needle, said mandrel having a head, complementary to said enlarged opening and slidable therein, when said device is in a protected configuration, said projection is in said hollow portion remote from said closed end and said needle extends into said hollow portion, when said device is in an operative configuration, said closed end is in said enlarged opening and bears against said head to urge said mandrel against said solid material toward said point.

* * * * *